United States Patent [19]

Porter et al.

[11] Patent Number: 5,569,665
[45] Date of Patent: Oct. 29, 1996

[54] PEPTIDYL DERIVATIVES AND THEIR USE AS METALLOPROTEINASES INHIBITORS

[75] Inventors: John R. Porter; John R. Morphy; Thomas A. Millican, all of Berkshire; Nigel R. A. Beeley, Oxfordshire, all of United Kingdom

[73] Assignee: Celltech Limited, Berkshire, United Kingdom

[21] Appl. No.: 185,781

[22] PCT Filed: Jun. 3, 1993

[86] PCT No.: PCT/GB93/01186

§ 371 Date: Jun. 27, 1994

§ 102(e) Date: Jun. 27, 1994

[87] PCT Pub. No.: WO93/24449

PCT Pub. Date: Dec. 9, 1993

[30] Foreign Application Priority Data

Jun. 3, 1992 [GB] United Kingdom .................. 9211706

[51] Int. Cl.⁶ .................. C07D 213/56; A61K 31/44
[52] U.S. Cl. .................. 514/357; 546/300; 546/336; 514/351
[58] Field of Search .................. 546/346, 347, 546/300, 336; 514/357, 351

[56] References Cited

U.S. PATENT DOCUMENTS

| | | | |
|---|---|---|---|
| 4,918,105 | 4/1990 | Cartwright et al. | 514/575 |
| 4,996,358 | 2/1991 | Handa et al. | 562/621 |

FOREIGN PATENT DOCUMENTS

| | | | |
|---|---|---|---|
| 0214639 | 3/1987 | European Pat. Off. | 514/357 |
| 0231081 | 8/1987 | European Pat. Off. | 514/357 |
| 0236872 | 9/1987 | European Pat. Off. | 514/575 |
| 0274453 | 7/1988 | European Pat. Off. | 514/357 |
| 90/05716 | 5/1990 | WIPO | 514/357 |
| 90/05719 | 5/1990 | WIPO | 562/621 |
| 91/02716 | 3/1991 | WIPO | 514/357 |

OTHER PUBLICATIONS

Wahl et al., "Biochemistry And Inhibition of Collagenase And Stromelysin", *Annual Reports in Medicinal Chemistry*, vol. 25:177–184, (1989).

*Primary Examiner*—Zinna Northington Davis
*Attorney, Agent, or Firm*—Foley & Lardner

[57] ABSTRACT

Metalloproteinase inhibitors are provided which are selective inhibitors of the action of gelatinase, and may be of use in the treatment of cancer to control the development of tumour metastases.

8 Claims, No Drawings

PEPTIDYL DERIVATIVES AND THEIR USE AS METALLOPROTEINASES INHIBITORS

This application is a 371 of PCT/GB93/01186 filed Jun. 3, 1993.

FIELD OF THE INVENTION

This invention relates to a novel class of peptidyl derivatives, to processes for their preparation and to their use in medicine.

BACKGROUND TO THE INVENTION

In normal tissues, cellular connective tissue synthesis is offset by extracellular matrix degradation, the two opposing effects existing in dynamic equilibrium. Degradation of the matrix is brought about by the action of proteinases released from resident connective tissue cells and invading inflammatory cells, and is due, in part, to me activity of at least three groups of metalloproteinases. These are the collagenases, the gelatinases (or type-IV collagenases) and the stromelysins. Normally these catabolic enzymes are tightly regulated at the level of their synthesis and secretion and also at the level of their extracellular activity, the latter through the action of specific inhibitors, such as $\alpha_2$-macroglobulins and TIMP (tissue inhibitor of metalloproteinase), which form inactive complexes with metalloproteinases.

The accelerated, uncontrolled breakdown of connective tissues by metalloproteinase catalysed resorption of the extracellular matrix is a feature of many pathological conditions, such as rheumatoid arthritis, corneal, epidermal or gastric ulceration; tumour metastasis or invasion; periodontal disease and bone disease. It can be expected that the pathogenesis of such diseases is llkely to be modified in a beneficial manner by the administration of metalloproteinase inhibitors and numerous compounds have been suggested for this purpose (for a general review see Wahl, R. C. et al Ann. Rep. Meal. Chem. 25, 175–184, Academic Press Inc., San Diego (1990).

Certain hydroxamic acid peptidyl derivatives (see for example European Patent Specifications Nos. 214639, 231081, 236872 and 274453 and International Patent Specifications Nos. WO90/05716 and WO90/05719), have been described as collagenase and/or stromelysin inhibitors.

SUMMARY OF THE INVENTION

We have now found a new class of peptidyl derivatives, members of which are metalloproteinase inhibitors and which, in particular, advantageously possess a potent and selective inhibitory action against gelatinase.

There is now much evidence that metalloproteinases are important in tumour invasion and metastasis. Tumour cell gelatinase, in particular, has been associated with the potential of tumour cells to invade and metastasise. Tumour invasion and metastasis is the major cause of treatment failure for cancer patients, and the use of a selective gelatinase inhibitor such as a compound of the present invention which is capable of inhibiting tumour cell invasion can be expected to improve the treatment of this disease.

Thus according to one aspect of the invention we provide a compound of formula (1)

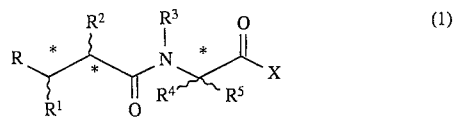

wherein R represents a —CONHOH, carboxyl (—CO$_2$H), esterified carboxyl or —P(O)(X$^1$R$^8$)X$^2$R$^9$ group, where X$^1$ and X$^2$, which may be the same or different is each an oxygen or a sulphur atom, and R$^8$ and R$^9$, which may be the same or different each represents a hydrogen atom or an optionally substituted alkyl, aryl, or aralkyl group.

R$^1$ represents a hydrogen atom or an optionally substituted alkyl, alkenyl, aryl, aralkyl, heteroaralkyl or heteroarylthioalkyl group;

R$^2$ represents an optionally substituted aryloxy, arylthio, aryloxyalkyl, arylthioalkyl, heteroaryl, heteroaralkyl, heteroaryloxy, heteroarylthio, heteroaryloxyalkyl or heteroarylthioalkyl group;

R$^3$ represents a hydrogen atom or an alkyl group;

R$^4$ represents a hydrogen atom or an alkyl group;

R$^5$ represents an optionally substituted alkyl or alkenyl group optionally interrupted by one or more —O— or —S— atoms or —N(R$^7$)— groups, (where R$^7$ is a hydrogen atom or a C$_{1-6}$alkyl group) or a group —(Alk)$_n$R$^6$ where Alk is an alkyl or alkenyl group optionally interrupted by one or more —O— or —S— atoms or —N(R$^7$)— groups, n is zero or an integer 1, and R$^6$ is an optionally substituted cycloalkyl or cycloalkenyl group;

X represents an amino (—NH$_2$), or substituted amino, hydroxyl or substituted hydroxyl group;

and the salts, solvates and hydrates thereof.

It will be appreciated that the compounds according to the invention can contain one or more asymmetrically substituted carbon atoms, for example those marked with an asterisk in formula (1). The presence of one or more of these asymmetric centres in a compound of formula (1) can give rise to stereoisomers, and in each case the invention is to be understood to extend to all such stereoisomers, including enantiomers and diastereoisomers, and mixtures, including racemic mixtures, thereof.

In the formulae herein, the ~line is used at a potential asymmetric centre to represent the possibility of R- and S-configurations the ▬ line and the ------- line to represent an unique configuration at an asymmetric centre.

In the compounds according to the invention, when the group R represents an esterified carboxyl group, it may be for example a group of formula —CO$_2$R$^{15}$ where R$^{15}$ is a straight or branched, optionally substituted C$_{1-8}$alkyl group such as a methyl, ethyl, n-propyl, i-propyl, n-butyl, i-butyl, s-butyl or t-butyl group; a C$_{6-12}$arylC$_{1-8}$alkyl group such as an optionally substituted benzyl, phenylethyl, phenylpropyl, 1-naphthylmethyl or 2-naphthylmethyl group; a C$_{6-12}$aryl group such as an optionally substituted phenyl, 1-naphthyl or 2-naphthyl group; a C$_{6-12}$aryloxyC$_{1-8}$alkyl group such as an optionally substituted phenyloxymethyl, phenyloxyethyl, 1-naphthyloxymethyl or 2-naphthyloxymethyl group; an optionally substituted C$_{1-8}$alkanoyloxyC$_{1-8}$salkyl group, such as a pivaloyloxymethyl, propionyloxyethyl or propionyloxypropyl group; or a C$_{6-12}$aroyloxyC$_{1-8}$alkyl group such as an optionally substituted benzoyloxyethyl or benzoyloxypropyl group. Optional substituents present on the groups R$^{15}$ include for example one or more halogen atoms such as fluorine, chlorine, bromine or iodine atoms, or C$_{1-4}$alkyl, e.g. methyl or ethyl, or C$_{1-4}$alkoxy, e.g. methoxy or ethoxy, groups.

In general, when the group R represents an esterified carboxyl group, it may be a metabolically lablie ester of a carboxylic acid.

When the group $R^1$ in compounds of formula (1). represents an optionally substituted alkyl or alkenyl group, it may be, for example, a straight or branched $C_{1-6}$ alkyl or $C_{2-6}$alkenyl group, such as a methyl, ethyl, n-propyl, i-propyl, n-butyl, i-butyl, s-butyl, t-butyl, n-pentyl, i-penty, n-hexyl, ethenyl, 1-propenyl, 1-butenyl or 2-butenyl group optionally substituted by one or more $C_{1-6}$alkoxy, e.g. methoxy, ethoxy, propoxy, $C_{1-6}$alkylthio, e.g. methylthio, ethylthio, propylthio, $C_{6-12}$aryl$C_{1-6}$ alkoxy, e.g. phenyl$C_{1-6}$ alkoxy such as benzyloxy, aralkylthio, e.g phenyl$C_{1-6}$alkylthio such as benzylthio, amino (—$NH_2$), substituted amino, [such as —$NHR^{16}$, where $R^{16}$ is a $C_{1-6}$ alkyl e.g. methyl or ethyl, $C_{6-12}$aryl$C_{1-6}$alkyl, e.g. phenyl$C_{1-6}$alkyl, such as benzyl, $C_{6-12}$ aryl, e.g. phenyl, $C_{3-8}$cycloalkyl, e.g. cyclohexyl, or $C_{3-8}$cycloalkyl$C_{1-6}$ alkyl, e.g. cyclohexylmethyl group], carboxyl (—$CO_2H$) or —$CO_2R^{15}$ [where $R^{15}$ is as defined above] groups.

Aryl groups represented by $R^1$ in compounds of formula (I) include $C_{6-12}$ aryl groups such as phenyl or 1- or 2-naphthyl groups.

Aralkyl groups represented by $R^1$ include $C_{6-12}$aryl$C_{1-6}$alkyl groups such as phenyl$C_{1-6}$alkyl, or 1- or 2-naphthyl$C_{1-6}$alkyl, for example benzyl, phenylethyl, phenylpropyl, phenylbutyl, phenylpentyl, 1- or 2-naphthylmethyl, naphthylethyl, naphthylpropyl, naphthylbutyl or naphthylpentyl groups.

When the group $R^1$ in compounds of formula (1) is a heteroaratkyl group, it may be for example a $C_{3-6}$heteroaryl$C_{1-6}$alkyl group, such as an optionally substituted pyrrolylmethyl, furanylmethyl, thienylmethyl, imidazolylmethyl, oxazolylmethyl, thiazolylmethyl, pyrazolylmethyl, pyridinylmethyl, or pyrimidinylmethyl group.

Heteroarylthioalkyl groups represented by $R^1$ include $C_{3-6}$heteroarylthio$C_{1-6}$alkyl groups such as optionally substituted pyrrolylthiomethyl, furanylthiomethyl, oxazolylthiomethyl, thiazolylthiomethyl, pyrazolylthiomethyl, pyridinylthiomethyt or pyrimidinylthiomethyl groups.

Optional substituents which may be present on heteroaralkyl or heteroarytthioalkyl groups represented by $R^1$ include those $R^{10}$ substituents discussed below.

When the group $R^2$ in the compounds according to the invention is an aryloxy, arylthio, aryloxyalkyl or arylthioalkyl group, the aryl portion of the group may be a $C_{6-12}$aryl group such as an optionally substituted phenyl, 1-naphthyl or 2-naphthyl group. The alkyl portion of such groups may be a straight or branched $C_{1-6}$alkyl group such as a methyl, ethyl, n-propyl, i-propyl, n-butyl, i-butyl, s-butyl, t-butyl, n-pentyl, i-pentyl or n-hexyl group.

When $R^2$ is a heteroaryl, heteroaralkyl, heteroarytoxy, heteroarylthio, heteroaryloxyalkyl or heteroarylthioalkyl group, the heteroaryl portion of each group may be a $C_{3-6}$heteroaryl group containing one, two or three heteroatoms, selected from —O— or —S—, or —$N(R^7)$— groups. Particular examples include optionally substituted pyrrolyl, furanyl, thienyl, imadazolyl, oxazolyl, thiazolyl, pyrazolyl, pyridinyl or pyrimidinyl groups. It will be appreciated that such groups may be connected to the remainder of the compound of formula (1) through any ring carbon atom or where appropriate through a heteroatom or group —$N(R^7)$—. The alkyl portion of any heteroaryl containing $R^2$ group may be a straight or branched $C_{1-6}$ group, e.g. a $C_{3-6}$ alkyl group, such as a methyl, ethyl, n-propyl, i-propyl, n-butyl, i-butyl, s-butyl, t-butyl, n-pentyl, i-pentyl or n-hexyl group.

The aryl, aralkyl, aryloxy, arylthio, aryloxyalkyl, arylthioalkyl, heteroaryl, heteroaralkyl, heteroaryloxy, heteroarylthio, heteroaryloxyalkyl or heteroarylthioalkyl groups represented by $R^1$ and/or $R^2$ in compounds of formula (1) may each optionally be substituted in the cyclic part of the group by one, two or more substituents ($R^{10}$) selected from halogen atoms, e.g. fluorine, chlorine, bromine or iodine atoms, or $C_{1-6}$alkyl, e.g. methyl or ethyl, $C_{1-6}$alkoxy e.g. methoxy or ethoxy, $C_{2-6}$alkylenedioxy, e.g. ethylenedioxy, halo$C_{1-6}$alkyl, e.g. tri-fluoromethyl, $C_{1-6}$alkylamino, e.g. methylamino or ethylamino, $C_{1-6}$dialkylamino, e.g. dimethylamino or diethylamino, amino (—$NH_2$), nitro, cyano, hydroxyl (—OH), carboxyl (—$CO_2H$), —$CO_2R^{15}$, where $R^{15}$ is as defined above, $C_{1-6}$alkylcarbonyl, e.g. acetyl, sulphonyl (—$SO_3H$), $C_{1-6}$alkylsulphonyl, e.g. methylsulphonyl, aminosulphonyl (—$SO_2NH_2$), $C_{1-6}$ alkylaminosulphonyl, e.g. methylaminosuiphonyl or ethylaminosulphonyl, $C_{1-6}$dialkylaminosulphonyl e.g. dimethylaminosulphonyl or diethylaminosulphonyl, carboxamido (—$CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, sulphonylamino (—$NHSO_2H$), $C_{1-6}$alkylsulphonylamino, e.g. methylsulphonylamino or ethylsuiphonylamino, $C_{1-6}$dialkylsuiphonylamino, e.g. dimethylsulphonylamino or diethytsulphonylamino $C_{1-6}$ alkanoylamin.e, e.g. acetylamino or $C_{1-6}$ alkanoylamino $C_{1-6}$ alkyl e.g. acetylaminomethyl groups. It will be appreciated that where two or more $R^{10}$ substituents are present. these need not necessarily be the same atoms and/or groups. The $R^{10}$ substituents may be present at any ring carbon atom away from that attached to the rest of the molecule of formula (1). Thus, for example, in phenyt groups any substituents may be present at the 2-, 3- or 4- 5- or 6-positions relative to the ring carbon atom attached to the remainder of the molecule.

When the groups $R^3$ and $R^4$ in compounds of formula (1) are alkyl groups, they may be for example $C_{1-6}$alkyl groups such as methyl or ethyl groups.

The group $R^5$ in compounds of formula (1) may be an optionatly substituted straight or branched $C_{1-6}$alkyl, e.g. methyl, ethyl, n-propyl, i-propyl, n-butyl, i-butyl, t-butyl, n-pentyl or n-hexyl or $C_{2-6}$alkenyl e.g. ethenyl or 1-propenyl group optionally interrupted by one or more —O— or —S— atoms or —$N(R^7)$— groups where $R^7$ is a hydrogen atom or a $C_{1-6}$alkyl group such as a methyl group.

Optional substitutents which may be present on alkyl or alkenyl groups $R^5$ include $C_{6-12}$aryl$C_{1-6}$alkyl groups such as optionally substituted phenyl$C_{1-6}$ alkyl e.g. benzyl groups, $C_{6-12}$aryl$C_{1-6}$alkoxy groups such as optionally substituted phenyl$C_{1-6}$alkoxy e.g. benzyloxy groups, $C_{6-12}$aryl e.g. optionally substituted phenyl groups, $C_{3-8}$heteroaryl e.g. optionally substituted indole, imidazole or quinoline groups, $C_{6-12}$aryl$C_{1-6}$alkoxy$C_{6-12}$ aryl, e.g. benzyloxyphenyl groups, —OH, —SH, $C_{1-6}$alkylthio e.g. methylthio or ethylthio, carboxy (—$CO_2H$), amino (—$NH_2$), carboxamido (—$CONH_2$)or guanido —$NHC(NH_2)$=NH, groups. The optional substituents present on these groups may be $R^{10}$ substituents as discussed above.

When the group Alk is present in compounds of formula (1) it may be a straight or branched $C_{1-6}$alkyl, e.g. methyl, ethyl, n-propyl i-propyl, n-butyl, i-butyl, t-butyl, n-pentyl or n-hexyl or $C_{2-6}$alkenyl e.g. ethenyl or 1-propenyl group optionally interrupted by one or more —O— or —S— atoms or —$N(R^7)$— groups where $R^7$ is a hydrogen atom or a $C_{1-6}$alkyl group such as a methyl group.

The group $R^6$ in compounds of formula (1) may represent a $C_{3-8}$cycloalkyl, e.g. cyclopentyl or cyciohexyl, or $C_{3-8}$cycloalkenyl e.g. cyclopentenyl or cyclohexenyl, group optionally substituted by one, two or more $C_{1-6}$alkyl, e.g. methyl or ethyl, $C_{1-6}$alkoxy, e.g. methoxy or ethoxy, $C_{1-6}$alkylthio, e.g. methylthio, or hydroxyl groups.

When X in the compounds of formula (1 represents a substituted amino group it may be for example a group of formula —$NR^{11}R^{12}$, where $R^{11}$ and $R^{12}$, which may be the same or different, is each a hydrogen atom (with the proviso that when one of $R^{11}$ or $R^{12}$ is a hydrogen atom, the other is not) or an optionally substituted straight or branched alkyl group, optionally interrupted by one or more —O— or —S— atoms or —$N(R)^7$— or aminocarbonyloxy (—NHC(O)O—) groups or $R^{11}$ and $R^{12}$, together with the nitrogen atom to which they are attached, may form an optionally substituted $C_{3-6}$cyclic amino group optionally possessing one or more other heteroatoms selected from —O—, —S—or—$N(R)^7$— groups.

When $R^{11}$ and/or $R^{12}$ is an alkyl group it may be for example a $C_{1-6}$alkyl group such as a methyl, ethyl, n-propyl, i-propyt, n-butyl, i-butyl, s-butyl, or t-butyl group, optionally interrupted by one or more —O— or —S— atoms, or —$N(R^7)$— or aminocarbonyloxy groups and may be for example a methoxymethyl, ethoxymethyl, methoxyethyl, ethoxyethyl or ethylaminocarbonyloxymethyl group. The optional substituents which may be present on such groups include hydroxyl (—OH), carboxyl (—$CO_2H$), esterified carboxyl (—$CO_2R^{15}$), carboxamido (—$CONH_2$), substituted carboxamido, e.g. a group —$CONR^{11}R^{12}$ where $NR^{11}R^{12}$ is as defined herein, amino (—$NH_2$), substituted amino, for example a group of formula —$NR^{11}R^{12}$, aminosulphonylamino, for example —$N(R^7)SO_2NH_2$ or —$N(R^7)SO_2NR^{11}R^{12}$, or aryl, e.g. $C_{6-12}$ aryl such as phenyl, optionally substituted by one, two or more $R^{10}$ substituents selected from those listed above in relation to the group $R^2$.

Particular examples of cyclic amino groups represented by —$NR^{11}R^{12}$ include morpholinyl, imidazolyl, piperazinyl, pyrrolyl, oxazolyl, thiazolyl, pyrazolyl, pyrrolidinyl, pyridinyl and pyrimidinyl groups.

The groups $R^8$ or $R^9$ in compounds of formula (1) may be hydrogen atom or an optionally substituted straight or branched $C_{1-6}$alkyl, e.g. methyl, ethyl, n-propyl, i-propyl, n-butyl or i-butyl, $C_{6-12}$aryl e.g. phenyl, or $C_{6-12}$aryl$C_{1-6}$alkyl, e.g. benzyl, phenylethyl or phenylpropyl group. Optional substituents present on alkyl groups of this type include one or more $C_{1-6}$alkoxy, e.g. methoxy, ethoxy, or $C_{1-6}$alkylthio e.g. methylthio or ethylthio groups or an optionally substituted $C_{6-12}$aryloxy, e.g. phenyloxy, $C_{6-12}$arylthio e.g. phenylthio, $C_{6-12}$aryl$C_{1-6}$alkoxy e.g. benzyloxy or $C_{6-12}$aryl$C_{1-6}$alkylthio e.g. benzylthio. Optional substituents present on the groups $R^8$ or $R^9$ when it is an aryl or aralkyl group or an alkyl group substituted by an aryloxy or arylthio group include Rio groups present on the cyclic part of $R^8$ or $R^9$ as defined above.

Salts of compounds of formula (1) include pharmaceutically acceptable salts, for example acid addition salts derived from inorganic or organic acids, such as hydrochlorides, hydrobromides, nyaroiodides, p-toluene sulphonates, phosphates, sulphates, acetates, trifluoroacetates, propionates, citrates, maleates, fumarates, malonates, succinates, lactates, oxalates, tartarares and benzoates.

Salts may also be formed with bases. Such salts include salts derived from inorganic or organic bases, for example alkali metal salts such as sodium or potassium salts, alkaline earth metal salts such as magnesium or calcium salts, and organic amine salts such as morpholine, piperidine, dimethylamine or diethylamine salts.

When the group R in compounds of the invention is an esterifiea carboxyl group, it may be a metabolically lablie ester of formula —$CO_2R^{15}$ where $R^{15}$ may be an ethyl, benzyl, phenylethyl, phenylpropyl, 1- or 2-naphthyl, 2,4-dimethylphenyl, 4-t-butylphenyl, 2,2,2-trifiuoroethyl, 1-(benzyloxy)benzyl, 1-(benzyloxy)ethyl, 2-methyl-1-propionyloxypropyl, 2.4,6-trimethylbenzoyloxymethyl or pivaloyloxymethyl group.

When the group R in compounds of formula (1) is a —$P(O)(X^1R^8)X^2R^9$ group it may in particular be a —$P(O)(OH)OR^9$, —$P(O)(SH)OR^9$ or —$P(O)(OH)SR^9$ group. Examples of such groups include —$P(O)(OH)OH$, —$P(O)(OH)SH$. —$P(O)(SH)OH$, —$P(O)(OH)OCH_3$, —$P(O)(OH)SCH_3$, —$P(O)(OH)OCH_2CH_3$. —$P(O)(OH)OPh$, —$P(O)(OH)SPh$, —$P(O)(OH)OCH_2Ph$ or —$P(O)(OH)SCH_2Ph$, where Ph is a phenyl group optionally substituted by one or more substituents $R^{10}$.

In the compounds of formula (1) the group $R^1$ may in particular De a $C_{1-6}$alkyl group such as a methyl group, an aralkyl group such as benzyl group, an arylthioalkyl group such as a phenythiomethyl group or a heteroarylthioalkyl group such as thienylthiomethyl, pyridinylthiomethyl or pyrimidinylthiomethyl group or is especially a hydrogen atom.

The group $R^2$ may be in particular an optionally substituted phenoxy, phenylthio, phenoxyalkyl, e.g. phenoxymethyl, pnenoxyethyl, phenoxypropyl, phenoxybutyl, phenylthioalkyl, e.g. phenylthiomethyl, phenylthioethyl, phenylthiopropyl, or phenylthiobutyl group or a group Het-, Het-oxy, Het-thio, Het-propyl, Het-butyl, Het-pentyl, Het-oxymethyl, Het-oxyethyl, Het-oxypropyl, Het-oxybutyl, Het-thiomethyl, Het-thioethyl, Het-thiopropyl or Het-thiobutyl, wherein Het is an optionally substituted pyrrolyl, furanyl, thienyl, imadazolyl, oxazolyl, thiazolyl, pyrazolyl, pyrimidinyl or, especially, pyridinyl group connected to the remainder of the group through a ring carbon atom or a heteroatom or —$N(R^7)$ group. Optional substituents present on $R^2$ groups of the above types include one, two or more $R^{10}$ substituents as defined above. Where the group is an optionally substituted phenyl group, it is preferably a 4-substituted phenyl group, for example a 4-halophenyl, e.g. 4-chlorophenyl, 4-alkoxyphenyl, e.g. 4-methoxyphenyl or 4-alkylphenyl, e.g. 4-methylphenyl group.

Particularly useful $R^2$ groups are aryloxyalkyl, heteroaralkyl or heteroraryloxyalkyl groups. Preferred groups of these types are optionally substituted phenoxyalkyl, e.g. phenoxyethyl, phenoxypropyl, or phenoxybutyl groups, Het-oxy $C_{1-6}$ alkyl such as pyridinyl-oxyethyl, pyridinyl-oxypropyl or pyridinyl-oxybutyl groups, or $C_{3-6}$ heteroaryl $C_{1-6}$ alkyl, e.g. $C_{3-6}$ heteroaryl $C_{3-6}$ alkyl such as $C_{3-6}$ heteroarylpropyl groups.

The groups $R^3$ and $R^4$ in compounds of formula (1), may each in particular be a methyl group, or, especially, a hydrogen atom.

The group $R^5$ in compounds of formula (1) may be in particular a group —$AlkR^6$, where $R^6$ is an optionally substituted cycloalkyl or cycloalkenyl group.

Thus, the group $R^5$ in compounds of formula (1) may be an optionally substituted $C_{3-8}$cycloalkyl$C_{1-6}$alkyl (e.g. cyclopentyl$C_{1-6}$alkyl such as cyclopentylmethyl or cyclopentylethyl, or cyclohexyl$C_{1-6}$alkyl such as cyclohexylmethyl or cyclohexylethyl), $C_{3-8}$cycloalkenyl$C_{1-6}$alkyl (e.g. cyclopentenyl$C_{1-6}$alkyl such as cyclopentenylmethyl or cyciohexenyl$C_{1-6}$ alkyl such as cyclohexenylmethyl), cycloalkyl$C_{1-3}$alkoxy$C_{1-3}$alkyl (e.g. cyclopentylmethoxymethyl, cyclohexylmethoxymethyl) $C_{3-8}$cycloalkenyl$C_{1-3}$ alkoxy$C_{1-3}$alkyl (e.g. cyclopentenylmethoxymethyl or cyclohexenylmethoxymethyl) $C_{3-8}$cycloalkyl$C_{1-3}$alkylthio$C_{1-3}$alkyl (e.g. cyclopentylmethylthiomethyl or cyclohexylmethylthiomethyl) or $C_{3-8}$ cycloalkenyl$C_{1-3}$alkylthio$C_{1-3}$alkyl (e.g. cyclopentenylmethylthiomethyl or cyclohexenylmethylthiomethyl), $C_{3-8}$cycloalky$C_{1-3}$alkylamino$C_{1-3}$alkyl (e.g. cyclopentenylmethylaminomethyl, or cyclohexylmethylaminomethyl) or $C_{3-8}$ cycloalkenyl$C_{1-3}$alkyamino$C_{1-3}$alkyl (e.g. cyclopentenylmethylaminomethyl or cyclohexenylmethylaminomethyl) group.

In another preference, the group $R^5$ in compounds of formula (1) may in particular be a $C_{1-6}$alkyl group, e.g. an i-propyl, i-butyl or t-butyl group, or an optionally substituted benzyl, benzyloxybenzyt or indolylmethyl group.

The group X in compounds of formula (1) may be in particular an amino (—$NH_2$) or —$NR^{11}R^{12}$ group. Particular —$NR^{11}R^{12}$ groups are —$NHR^{12}$ groups. Groups of this type include those where $R^{12}$ is a $C_{1-6}$alkyl group, for example a methyl, ethyl, or n-propyt group, optionally interrupted by one or more —O— or —S— atoms or —N($R^7$) (e.g. —NH— or —N($CH_3$)-) or aminocarbonyloxy groups and optionally substituted by a hydroxyl, carboxyt, carboxyalkyl, e.g. carboxymethyl, carboxamido, amino, —$NR_{11}R^{12}$, (for example di-$C_{1-6}$alkylamino such as dimethylamino, $C_{1-6}$alkylamino such as methylamino, or $C_{3-6}$cyctic amino such as morpholinyl, pyrrolidinyl or pyridinyl) aminosulphonylamino (for example —N($R^7$)$SO_2NH_2$ such as —$NHSO_2NH_2$, —N($CH_3$)$_3SO_2NH_2$ or —N($R^7$)$SO_2NR^{11}R^{12}$ such as —$NHSO_2R^{11}R^{12}$ or —N($CH_3$)$SO_2NR^{11}R^{12}$, especially where $R^{11}$ and $R^{12}$ is each an optionally substituted $C_{1-6}$alkyl group or $R^{11}$ and $R^{12}$ together with the nitrogen atom to which they are attached is an optionally substituted $C_{3-6}$ cyclic amino group) or phenyl optionally substituted by one, two or more $R^{10}$ substituents.

A particularly useful group of compounds according to the invention is that of formula (1) wherein $R^5$ is an Alk$R^6$, group, where Alk is a $C_{1-6}$alkyl and $R^6$ is a cycloalkyl or cycloatkenyl group.

In another preference, compounds of formula (1) wherein $R^5$ is a propyl, e.g. i-propyl or butyl, e.g. i-butyl or especially t-butyl group are particularly useful.

In general, in compounds of formula (1) the groups $R^1$, $R^3$ and $R^4$ is each preferably a hydrogen atom.

In a further preference, the group R in compounds according to the invention is a —CONHOH or a —$CO_2H$ group or a metabolically labile ester thereof, or a group P(O)(OH)$OR^7$. In a particular preference, however, R is a —$CO_2H$ or —P(O)(OH)$_2$ group or especially a —CONHOH group.

X in the compounds of formula (1) is preferably an amino or substituted amino group.

An especially useful group of compounds according to the invention has the formula (1a):

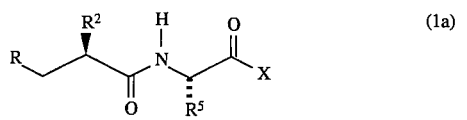

wherein R, $R^2$, $R^5$ and X are as defined for formula (1); and the salts, solvates and hydrates thereof.

It will be appreciated that the particular definitions and preferences recited above with respect to the groups R, $R^2$, $R^5$ and X also apply to these groups in compounds of formula (1a). In addition, a particularly useful group of compounds of formula (1a) are those wherein R represents a —CONHOH, or —$CO_2H$ or —P(O)(OH)$_2$ group; $R^2$ is as defined for formula (1);

$R^5$ represents a group —Alk$R^6$, where Alk is a $C_{1-6}$ alkyl group and $R^6$ is a cycloalkyl or cycloalkenyl group or a $C_{1-6}$ alkyl group;

X is an amino or substituted amino group; and the salts, solvates and hydrates thereof.

Particularly useful compounds of formula (1a) are those wherein $R^5$ is a group —Alk$R^6$, and $R^6$ is an optionally substituted cyclohexyl group. Compounds of this type in which $R^5$ is a cyclohexyl$C_{1-6}$alkyl group, particularly a cyclohexylmethyl group, are especially useful.

In another preference, compounds of formula (1a) wherein $R^5$ is a propyl, e.g. i-propyt or especially butyl, e.g. t-butyl, are particularly useful.

In the compounds of formula (1a) X may be a —$NH_2$ or —$NR^{11}R^{12}$ group.

In the compounds of formulae (1) and (1a), when the group $R^5$ is a cycloalkyl$C_{1-6}$alkyl group then the chiral centre to which this group is attached preferably has a S-configuration.

Particularly useful compounds according to the invention are:

{4-(N-hydroxyamino)-2(R)-(3-(4-pyridinium)propyl)succinyl}-L-β-cychlohexylalanine-N-(2-phenylethyl)amide;

{4-(N-hydroxyamino)-2(R)-(3-(4-pyridinium)propyl)succinyl}-L-β-cyclohexylalanine-N(2-(p-sulphonamidophenyl)ethyl)amide;

{4-(N-hydroxyamino)-2(R)-(3-(4-pyridinium)propyl)succinyl}-L-t-leucine amide;

{4-(N-hydroxyamino)-2(R)-(3-(2-phenoxyethyl)succinyl}-L-β-cyclohexylalanine-N-( 2-phenylethyl)amide; and the salts solvates and hydrates thereof.

The compounds according to the invention may be pareparecl by tlne following processes. In the description and formulae below the groups R, $R^1$, $R^2$, $R^3$, $R^4$, $R^5$ and X are as defined above, except where otherwise indicated. It will be appreciated that functional groups, such as amino, hydroxyl or carboxyt groups, present in the various compounds described below, and which it is desired to retain, may need to be in protected form before any reaction is initiated. In such instances, removal of the protecting group may be the final step in a particular reaction. Suitable amino or hydroxyl protecting groups include benzyl, benzyloxycarbonyl or t-butyloxycarbonyl groups. These may be removed from a protected derivative by catalytic hyclrogenation using for example hydrogen in the presence of a metal catalyst, for example palladium on a support such as carbon in a solvent such as an alcohol e.g. methanol, or by treatment with trimethylsilyl iodide or trifluoroacetic acid in an aqueous solvent. Suitable carboxyl protecting groups include benzyt groups, which may be removed from a protected derivative by the methods just discussed, or alkyl groups, such as a t-butyl group which may be removed from a protected derivative by treatment with trifluoroacetic acid in an aqueous solvent. Other suitable protecting groups and methods for their use will be readily apparent. The formation of the protected amino, hydroxyl or carboxyl group may be achieved using standard alkylation or esterification procedures, for example as described below.

Thus according to a further aspect of the invention a compound of formula (1) may be prepared by coupling an acid of formula (2)

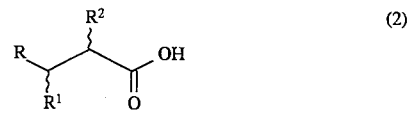

or an active derivative thereof, with an amine of formula (3)

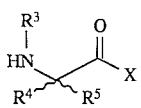

followed by removal of any protecting groups.

Active derivatives of acids for formula (2) include for example acid anhydrides, or acid halides, such as acid chlorides.

The coupling reaction may be performed using standard conditions for amination reactions of this type. Thus, for example the reaction may be achieved in a solvent, for example an inert organic solvent such as an ether, e.g. a cyclic ether such as tetrahydrofuran, an amide e.g. a substituted amide such as dimethylformamide, or a halogenated hydrocarbon such as dichloromethane at a low temperature, e.g. −30° C. to ambient temperature, such as −20° C. to 0° C., optionally in the presence of a base, e.g. an organic base such as an amine, e.g. triethylamine or a cyclic amine such as N-methylmorpholine. Where an acid of formula (2) is used, the reaction may additionally be performed in the presence of a condensing agent, for example a diimide such as N,N'-odicyclohexylcarbodiimide or 1-( 3-dimethylaminopropyl)-3-ethylcarbodiimide hydrochloride, advantageously in the presence of a triazole such as 1-hydroxybenzotriazole. Alternatively, the acid may be reacted with a chloroformate for example ethylchloroformate, prior to reaction with the amine of formula (3).

Free hydroxyl or carboxyl groups in the starting materials of formulae (2) and (3) may need to be protected during the coupling reaction. Suitable protecting groups and methods for their removal may be those mentioned above. Where R in the intermediates of formula (2) is a —P(O)(X$^1$R$^8$)X$^2$R$^9$ group, at least one of R$^8$ or R$^9$ is other than a hydrogen atom. Conveniently, each of R$^8$ and R$^9$ is a optionally substituted alkyl, aryl or aralkyl group. Such groups, when present in compounds of the invention may be cleaved as described below to yield other compounds of the invention wherein R$^8$ and/or R$^9$ is each a hydrogen atom.

When a particular stereoisomer of formula (1) is required, the resolution of a mixture of isomer is the same as described in WO 92/09564.

Where desired, however, appropriate homochiral starting materials may be used in the coupling reaction to yield a particular stereo isomer of formula (1). Thus, in a particular process a compound of formula (1a) may be prepared by reaction of a compound of formula (2a)

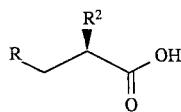

with an amine of formula (3a)

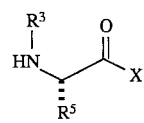

as described above

Intermediate acids of formula (2) wherein R is a or a group —P(O)(X$^1$R$^8$)X$^2$R$^9$ may be prepared from a corresponding ester of formula (4)

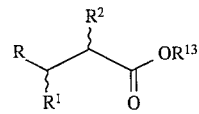

where R$^{13}$ is an alkyl group, for example a methyl or t-butyl group, by hydrolysis using for example trifluoroacetic acid, or, when R$^{13}$ is an aralkyl group, such as a benzyl group, by hydrogenolysis, for example by reaction with hydrogen in the presence of a metal catalyst, e.g. palladium, on a support such as carbon in a solvent such as an alcohol, e.g. methanol optionally at an elevated pressure and temperature.

Intermediate esters of formula (4) where R is a —P(O)(X$^1$R$^8$)X$^2$R$^9$ group may be prepared by reaction of an acrylate R$^1$CHC(R$^2$)COR$^{13}$ with a phosphite —P(OR$^{14}$)(X$^1$R$^8$)X$^2$R$^9$ where R$^{14}$ is a leaving group, for example a silyl group such as a trialkylsilyl group e.g. a trimethylsilyl group at an elevated temperature.

Acrylates of formula R$^1$CHC(R$^2$)COOR$^{13}$ may be prepared by reaction of a mono-ester HOOCCH(R$^2$)COOR$^{13}$ with an aldehyde R$^1$CHO or a polymer thereof e.g. paraformaldehyde or paraldehyde in the presence of a base. for example an organic base such as piperidine. The reaction may be performed in a solvent, such as pyridine, optionally at an elevated temperature.

Mono-esters of formula HOOCCH(R$^2$)COOR$^{13}$ may be prepared by hydrolysis of the corresponding di-ester R$^{13}$OOCCH(R$^2$)COOR$^{13}$ using a base, for example an alkali hydroxide, in an inert solvent such as dioxan at a low temperature e.g. around 0° C. The di-esters for use in this reaction may be prepared by alkylation of the corresponding malonates of formula R$^{13}$OOCCH$_2$COOR$^{13}$ with a halide R$^2$Hal (where Hal is a halogen atom such as a chlorine or bromine atom) in the presence of a base, e.g. a hydride such as sodium hydride in a solvent such as tetrahydrofuran at ambient temperature. Malonates of formula R$^{13}$OOCCH$_2$COOR$^{13}$ are either known compounds or may be prepared by methods analogous to those used for the preparation of the known compounds.

Intermediate phosphites of formula —P(OR$^{14}$)(X$^1$R$^8$)X$^2$R$^9$ may be prepared by reaction of a phosphite —P(O)(X$^1$R$^8$)X$^2$R$^9$ with an appropriate amine (R$^{14}$)$_2$NH e.g. a silazane, at an elevated temperature, e.g. the reflux temperature. Phosphites of formula P(O)(X$^1$R$^8$)X$^1$R$^9$ are either known compounds or may be prepared by methods analogous to those used for the preparation of the known compounds.

Intermediate amines of formula (3) may be prepared by reaction of the corresponding acids R$^3$NHC(R$^4$)(R$^5$)COOH or active derivatives thereof with an amine XH using the reagents and conditions described above for the preparation of compounds of formula (1) from intermediates for formula (2) and (3). The acids R$^3$NHC(R$^4$)(R$^5$)COOH and amines XH are either known compounds or may be prepared from known starting materials using analogous processes (for example as described in the preparation of the specific Intermediates in the Examples herein) to those used for the preparation of the known compounds.

The homochiral acids of formula (2a) may be prepared according to another feature of the invention by oxidation of an oxazolidinone of formula (5)

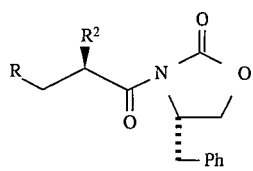

(where Ph is a phenyl group)

using an oxidising agent such as peroxide, e.g. hydrogen peroxide in a solvent such as an ether e.g. a cyclic ether such as tetrahydrofuran, at a low temperature, e.g. around 0° C. followed by treatment with a base, such as lithium hydroxide, at an elevated temperature.

The compounds of formula (5) are novel, particularly useful, intermediates for the preparation of stereoisomers of formula (1a) and form a further aspect of the invention.

The compounds of formula (5) may be prepared by reaction of an acyl halide $(R^2)COHal$ (where Hal is a halogen atom such as chlorine, bromine or iodine atom) with a solution of (S)-4-(phenylmethyl)-2-oxazolidinone in the presence of a base such as n-butyl lithium in a solvent such as tetrahydrofuran at a low temperature, e.g. around −78° C., followed by treatment of the resulting oxazolidinone with a reagent $RCH_2Hal$ in the prescence of a silazide such as sodium hexamethyldisilazide at a low temperature.

Acyl halides $R^2COHal$ may be prepared by treatment of the corresponding known acids $R^2CO_2{}^H$ with conventional halogenating agents for example thionyl halides such as thionyl chloride under standard reaction conditions.

In an other process, compounds of formula (5) wherein $R^2$ is a heteroarylpropyl group may be prepared by reaction of an acid $R^2CH_2CO_2H$ (wherein $R^2$ is as just defined) with a solution of (S)-4-(phenytmethyl)-2-oxazolidinone in the presence of a condensing agent such as dicychohexylcarbodiimide or N,N-dimethylaminopyridine. The acid itself may be prepared by hydrolysis of the corresponding ester $R^2CH_2CO_2R^{13}$ using well known methods, for example by treatment with lithium hydroxide in methanol at room temperature.

Esters $R^2CH_2CO_2R^{13}$ may be prepared by catalytic reduction of a diene of formula (6)

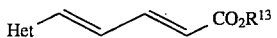

(wherein Het is a heteroaryt group as defined above for $R^2$) using standard methods, for example by catalytic hydrogenation using for example hydrogen in the presence of a catalyst such as palladium on carbon in a solvent such as methanol.

The diene of formula (6) may be prepared by coupling an aidehyde HetCHO with a phosphonate such as trimethylphosphonocrotonate in the presence of a silazide such as sodium hexamethyldisilizide in tetrahydrofuran at a temperature of about 0° C.

Compounds of formula (1) may also be prepared by interconversion of other compounds of formula (1). Thus, for example, a compound of formula (1) wherein R is a —CONHOH group may be prepared by reaction of a corresponding acid of formula (1) wherein R is a —$CO_2H$ group or an active derivative thereof (for example an acid chloride or an acid anhydride) with hydroxylamine or an O-protected derivative for example O-trimethylsilylhydroxylamine or a salt thereof. The reaction may be performed using the reagents and conditions described above in the preparation of compounds of formula (1) from the staring materials of formulae (2) and (3). If desired the acid starting material may be reacted with a chloroformate, for example ethyl chloroformate, prior to reaction with the hydroxylamine or protected hydroxylamine.

In another interconversion process, compounds of formula (1) wherein R is —$CO_2H$ may be prepared by hydrolysis of the corresponding esterified compounds (for example where R is a —$CO_2R^{15}$ group and/or X contains a similar group) using conventional procedures, for example by treatment with a base, e.g. an alkali metal hydroxide such as lithium hydroxide in a solvent such as an aqueous alcohol, e.g. aqueous methanol, or by treatment with an acid such as a mineral acid, e.g. hydrochloric acid in the presence of a solvent, e.g. dioxan.

Similarly esters of formula (1) for example where R is a $CO_2R^{15}$ group and/or X contains a —$CO_2R^{15}$ group may be prepared by reaction of the corresponding acids, where R is a —$CO_2H$ group and/or X contains a —$CO_2H$ group or an active derivative thereof, with an alcohol $R^{15}OH$ using standard conditions.

The compounds according to the invention are potent and selective inhibitors of gelatinase. The activity and selectivity of the compounds may be determined by the use of appropriate enzyme inhibition test for example as described in Example A hereinafter. In our tests using this approach, compounds according to the invention have been shown to inhibit gelatinase with Ki values in the picomolar-nanomolar range and to have around a 40 fold or greater selectivity for gelatinase over stromelysin, and around a 100-fold or greater selectivity for gelatinase over collagenase.

The ability of compounds of the invention to prevent tumour cell invasion may be demonstrated in a standard mouse model.

Thus, briefly, nude mice may be inoculated with a tumour cell line showing gelatinase—dependent invasion and the ability of compounds according to the invention to reduce subsequent lung tumour colonisation may be evaluated in accordance with standard procedures. In out tests, compounds according to the invention, when administered intravenously at 1 mg/kg to mice in the above model have reduced lung rumour colonisation to negligable levels.

The compounds according to the invention can be expected to be of use to prevent tumour cell metastasis and invasion. The compounds may therefore be of use in the treatment of cancer, particularly in conjunction with radiotherapy, chemotherapy or surgery, or in patients presenting with primary turnours, to control the development of tumour metastases. Thus, according to a further aspect of the invention we provide a compound of formula (1) for use in the treatment of cancer to control the development of turnour metastases. Particular cancers may include breast, melanoma, lung, head, neck or bladder cancers.

For use according to this aspect of the invention, the compounds of formula (1) may be formulated in a conventional manner, optionally with one or more physiologically acceptable carriers, diluents or excipients.

Thus according to a further aspect of the invention we provide a pharmaceutical composition comprising a compound of formula (1) and a pharmaceutically acceptable diluent, carrier or excipient.

In a still further aspect the invention provides a process for the production of a pharmaceutical composition comprising bringing a compound of formula (1) into association with a pharmaceutically acceptable diluent, carrier or excipient.

Compounds for use according to the present invention may be formulated for oral, buccai, parental or rectal administration or in a form suitable for nasal administration or administration by inhalation or insuffiation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles; and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formula (1) may be formulated for parental administration by injection e.g. by bolus injection or continuous infusion. Formulations for injection may be presented in unit dosage form. The compositions for injection may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of formula (1) may also be formulated in rectal compositions such as suppositories or retention enemas, e.g. containing conventional suppository bases such as cocoa butter or other glycerides.

In addition to the formulations described above the compounds of formula (1) may also be formulated as a depot preparation. Such long acting formulations may be administered by implantation or by intramuscular injection.

For nasal administration or administration by inhalation the compounds for use according to the present invention are conventiently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas.

The compositions may, if desired, be presented in a pack or dispenser device which may contain one or more unit dosage forms containing the active ingredient. The pack or dispenser device may be accompanied by instructions for admininstration.

The doses of compounds of formula (1) used to control the development of tumour metastases will vary depending on the condition of the patient to be treated but in general may be in the range around 0.5 mg to 100 mg/kg body weight, particularly from about 1 mg to 40 mg/kg body weight. Dosage units may be varied according to the route of administration of the compound and condition of the patient in accordance with conventional practice.

The following Examples illustrate the invention.

Example A

The activity and selectivity of the compounds of the invention may be determined as described below.

All enzyme assays to determine Ki values were performed using the peptide substrate Dnp-Pro-Leu-Gly-Trp-Ala-D-Arg-NH$_2$. (M. Sharon Stock and Rober D. Gray, JBC 264, 4277–81, 1989). The enzymes cleave at the Gly-Leu bond which can be followed fluorimetrically by measuring the increase in Trp fluorescence emission associated with the removal of the quenching dinitrophenol (Dnp) group.

Essentially, enzyme (e.g. gelatinase, stromelysin, coilagenase) at 0.08–2 nM; a range of inhibitor concentrations (0.1–50×Ki) and substrate (approx. 20 µm) are incubated overnight in 0.1M Tris/HCl buffer, pH 7.5, containing 0.1M NaCl, 10 mM CaCl$_2$ and 0.05%. Brij 35 at either room temperature or 37° C. depending on the enzyme. The reaction is stopped by adjusting the pH to 4 using 0.1M sodium acetate buffer and the fluorescence read at an excitation wavelength of 280nm and emission wavelength of 346nm.

$K_i$ values can be established using the equation for tight-binding inhibition:

$$V_i = \frac{V_o}{2[E]} \left( \sqrt{(K_{i(app)} + [I])^2 + 2(K_{i(app)} - [I])[E] + [E]^2} - (K_{i(app)} + [I] - [E]) \right)$$

where $V_o$ is the initial rate of reaction in the absence of inhibitor, $V_i$ is the initial rate in the presence of inhibitor, [E] is the total enzyme concentration and [I] the total inhibitor concentration in the reaction mixture.

For stromelysin and collagenase, $K_i$ (app) was assumed to approximate to the true $K_i$ as $[S] \ll K_m$ for the substrate hydrolysis. For gelatinase the $K_i$ was determined by performing the analyses at several substrate concentrations. A plot of $K_i$(app) vs. [S] then gave the true $K_i$ as the value of the y-axis intercept.

The following results were obtained with compounds according to the invention

| Compound of Example No. | Ki (nM) | | |
| --- | --- | --- | --- |
| | Collagenase | Stromelysin-1 | Gelatinase –72 KD |
| 2 | 48800 | 1510 | 22.2 |
| 3 | 478 | 29.7 | 0.273 |
| 5 | 186 | 12.6 | 0.035 |
| 6 | 22000 | 681 | 8.42 |
| 8 | 215 | 11.8 | 0.059 |

DESCRIPTION OF SPECIFIC EMBODIMENTS

The invention is further illustrated in the following non-limiting Examples.

In the Examples, the following abbreviations are used:

| | |
| --- | --- |
| RT | room temperature |
| DCCl | N,N'-dicyclohexylcarbodiimide |
| DMF | dimethylformamide |
| THF | tetrahydrofuran |
| TFA | trifluoroacetic acid |
| hplc | high performance liquid chromatography |
| Et$_2$O | diethylether |
| CH$_2$Cl$_2$ | dichloromethane |
| EtOAc | ethyl acetate |
| MeOH | methanol |
| iPr$_2$O | diisopropyl ether |
| All temperatures are in °C. | |

Intermediate 1

3(4-Phenoxybutanoyl)-4(S)-benzyl-2-oxlazilidinone

Phenoxybutyric acid (1.22 g, 6.8 mmol, 1.2 equiv) was heated to reflux with thionyl chloride (0.66 ml, 1.07 g, 9.0 mmol, 1.6 equiv) for 30 mins. The excess thionyl chloride was then removed under vacuum, the residue dissolved in THF (10 ml), and added to a cold (−78° C.) solution of lithiated (S)-4-benzyl-2-oxazilidinone (prepared from the oxazilidinone (1 g, 5.6 mmol) and n-butyl lithium (1.6M solution, 4.23 ml, 6.8 mmol, 1.2 equiv) in THF (25 ml). The reaction mixture was stirred for 2 hrs at −78° C., then quenched with a 1:1 mixture of saturated brine and 10% HCl acid (20 ml). The mixture was allowed to warm to room temperature and partitioned between EtOAc and water. The layers were separated and the aqueous layer washed twice with EtOAc. The combined organic layers were washed once with brine, once with sodium bicarbonate solution, dried over $MgSO_4$ and the solvent removed under vacuum to give a brown oil which was recrystallised from EtOAc to give the title compound as a white solid (0.897 g).

$^1$H NMR $CDCl_3$ δ: 7.35-7.17 (m 7H); 6.94-6.86 (m, 3H); 4.66 (m, 1H); 4.18 (m, 2H); 4.06 (t, 2H); 3.30 (dd, 1H); 3.16 (t, 2H); 2.25 (dd, 1H); 2.18 (m, 2H).

Intermediate 2

3-[1-oxo-2(R)(t-butyl-acetyl-5-(phenoxy)propyl)-4(S)-benzyl-2-oxazolidinone

Sodium hexamethyldisilazide (1.0M solution in THF, 4.2 ml, 4.2 mmol, 1.4 equiv) was added dropwise to a solution of Intermediate 1. (1.01 g, 3 mmol) in THF (25 ml) at −78C. Stirring was continued at this temperature for 1 hr, then t-butyl bromoacetate (1.74 g, 1.44 ml, 9 mmol, 3 equiv) was added. The temperature was allowed to rise to −20° C. over a period of 4 hrs. The reaction was then cooled to −78° C. and quenched with a mixture of brine and 10% HCl acid (1:1, 20 ml). The reaction was warmed to room temperature and partitioned between water and EtOAc. The aqueous layer was washed twice with EtOAc and the combined organic layers washed once with sodium bicarbonate solution, once with brine, dried over $MgSO_4$ and the solvent removed in vacuo to give a yellow oil, which was purified on Silica gel (Merck 9385) eluting with 25% EtOAc/hexane to give the title compound as a white solid, (0.90 g).

$^1$H NMR $CDCl_3$δ: 7.40-7.18 (m, 7H); 6.95-6.80 (m, 3H); 4.62 (m, 1H); 4.42 (m, 1H); 4.28.-3.96 (m, 3H); 3.87 (t, 1H); 3.33 (dd, 1. H); 2.91 (dd, 1H); 2.72 (dd, 1H); 2.56 (dd, 1H); 2.26-1.94 (m, 2H); 1.42 (s, 9H).

Intermediate 3

2-(R)-(3-(2-Phenoxyethyl))succinic acid-4-t-butyl monoester

Hydrogen peroxide (0.91 ml, 8 mmol, 4 equiv 27.5 wt %) was added to a cold (0° C.) solution of Intermediate 2 (0.9 g, 2 mmol) in THF/water (4:1, 50 ml). The solution was stirred for 5 mins then a solution of lithium hydroxide (80 mg, 2mmol) in water (10ml) was added dropwise. The reaction was stirred for 2 hours at 0° C. then most of the THF was removed in vacuo. The mixture was partitioned between water and $CH_2Cl_2$, and the aqueous layer separated, acidified to pH1 with 10% HCl acid and extracted, with EtOAc (x3). The combined organic layers were dried over $MgSO_4$ and the solvent removed to give the title compound as a colourless oil, (0.60 g, quantitative), which was used without further purification.

Intermediate 4

L-β-cyclohexylanine-N-(2-phenylethyl) amide t-Boc-β-cyclohexyl-L-alanine (1.35 g, 5 mmol) was dissolved in dry $CH_2Cl_2$. 4-Nitrophenol (695 mg, 5 mmol) was added followed by DCCI (1.03 g, 5 mmol). After 1 hour at room temperature the reaction was concentrated in vacuo, $Et_2O$ was added and the solution filtered. The residue was concentrated in vacuo, dissolved in $CH_2Cl_2$ (10 ml) and phenethylamine (690 μl, 5.5 mmol) was added. The reaction was poured into sodium bicarbonate solution and extracted with $CH_2Cl_2$ (3×20 ml), was dried ($Na_2SO_4$) and concentrated in vacuo.

Purification on silica gel (Merck 9385) using $CH_2Cl_2$—$CH_2Cl_2$/MeOH (85:15) gave a clean oil (900 mg) which was concentrated in vacuo dissolved in $CH_2Cl_2$ (50 ml) and poured into sodium bicarbonate solution. The organic layer was separated, dried ($Na_2SO_4$) and concentrated in vacuo to give an oil which was purified on silica gel (Merck 9385) using $CH_2Cl_2$/MeOH/triethytamine (96:3.1) to give the title compound as an oil (500 mg).

$^1$H NMR $CDCl_3$δ: 0.95 (m, 2H); 1.25 (m, 6H); 1.55 (br s, 2H); 1.65 (m, 5H);, 2.8 (t, 2H, J=6 HZ); 3.4 (dd, 1H, J=3 and 10 HZ); 3.5 (dd, 2H, J=6 and 12 HZ); 7.2 (m, 5H).

Intermediate 5

Methyl-4-(4-pyridyl)-buta-1,3-diene carboxylate

Sodium hexamethyldisilazide (23 ml,1.0M solution in THF, 23 mmol, 1.2 equiv) was added to a cold (0° C.) solution of trimethyl phosphonocrotonate (4.00 g, 19.2 mmol) in THF (60 ml) under a $N_2$ atmosphere. The solution was warmed to room temperature during which time a gummy brown precipitate was formed. After stirring for 30 mins the reaction was cooled to 0° C. and 4-pyridine carboxaldehyde (2.06 g, 1.83 ml, 19.2 mmol, 1 equiv)was added dropwise. The reaction was warmed to room temperature and stirred for 4 h. The reaction was then poured into ice water and extracted seven times with EtOAc. The combined organic layers were dried over $MgSO_4$, the solvent removed under vacuum to give a red/brown gummy solid which was recrystallised from MeOH/water to give the title compound (1.01 g).

$^1$Hnmr,$CD_3$OD δ: 8.51 (d, 2 H, CHN); 7.53 (d, 2H, CHCHN);7.46-7.22 (m, 2H, CH=); 6.95 (d, 2H); 6.18 (d, 2H); 3.76 (s, 3H).

Intermediate 6

Methyl-4-(4-pyridyl)-butane carboxylate

Palladium on carbon (ca 30 mg) was added to a degassed solution of Intermediate 5 (1.94 g, 10.3 mmol) in MeOH (20 ml) and stirred under a $H_2$ atmosphere for 12 h. The reaction mixture was filtered through a silica pad and the residue was washed several times with MeOH. The washings were combined and the solvent removed under vacuum to give the title compound as a brown oil (1.94 g).

$^1$Hnmr $CD_3$OD δ: 8.41 (dd, 2H); 7.28 (dd, 2H); 3.64 (s, 3H); 2.67 (t, 2H); 2.37 (t,2H); 1.68 (m, 4H).

Intermediate 7

5-(4-pyridyl)valeric acid

Lithium hydroxide monohydrate (1.26 g, 30.1 mmol, 3 equiv) was added to a solution of Intermediate 6 (1.94 g, 10.1 mmol) in MeOH (25 ml) and stirred at room temperature for 4 h under a $N_2$ atmosphere. After this time the solution was acidified to pH5 with 10% HCl acid and the off white precipitate removed by filtration, washed once with

Intermediate 8

(S)-3(1-oxo-5-(4-pyridyl)pentyl)-4-(phenylmethyl)-2-oxazolidinone

A solution of Intermediate 7 (0.63 g, 3.52 mmol), (S)-4-phenylmethyl-2-oxazolidinone (0.56 g, 3.17 mmol), DCCl (0.91 g, 4.4 mmol, 1.25 equiv) and N,N-dimethylaminopyridine (0.22 g, 1.8 mmol, 0.5 equiv) was heated to reflux for 18 h under $N_2$. After this time the reaction mixture was filtered and the solvent removed under vacuum. The product was purified on silica gel (Merck 9385) eluting with EtOAc/hexane (95:5) to give the title compound as a colourless oil (0.71 g).

$^1$Hnmr $CD_3OD$ δ8.40 (dd, 2H, J=1.5, 4.5 Hz); 7.32-7.18 (m, 7H); 4.72 (m, H); 4.32-4.18 (m, 2H); 3.11 (dd, 1H, J=3.3, 13.5 Hz); 2.91 (m, 3H); 2.70 (m, H); 1.72 (m, 4H).

Intermediate 9

3-(1-oxo-2(R)-(t-butylacetyl)-5-(4-pyridyl)pentyl)-4-(S)-phenyl methyl-2-oxazolidinone Sodium hexamethyldisilazide (1.95 ml of 1M solution in THF, 1.95 mmol, 1.2 equiv) was added clropwise to a solution of Intermediate 8 (0.55 g, 1.63 mmol) in THF (25 ml) at −78° C. under $N_2$. The reaction was stirred at −78° C. for 30 mins then a solution of t-Butylbromoacetate (0.32 g, 0.26 ml, 1.63 mmol, 1 equiv) in THF (5 ml) was added dropwise and the reaction stirred at −78° C. for 4 h, then warmed to −20° C. for 30 mins. The reaction was quenched at −78° C. with a saturated $NH_4Cl$ solution (10 ml). The reaction was warmed to room temperature and partitioned between EtOAc and water. The aqueous layer was extracted twice with EtOAc then the combined organic layers washed with brine, dried over $MgSO_4$ and the solvent removed to give 0.76 g of a yellow oil, which was purified in silica gel (Merck 9385) eluting with EtOAc (100%) to give the title compound as a colourless oil (0.53 g)

$^1$Hnmr $CD_3OD$ δ:8.38 (dd,2H, J=1.35, 4.6); 7.33-7.21 (m, 7H); 4.69 (m, 1H); 4.26-4.12 (m, 3H); 3.14 (dd, 1H, J=3.2m 13.5Hz); 2.89-2.63 (m, 4H); 2.49 (dd, 1H, J=4.7, 16.5 Hz); 1.79-1.57 (m, 4H); 1.42 (s, 9H).

Intermediate 10

2-(R)-(3-(4-pyridyl)propyl)succinic acid-4-t-butyl monoester

Hydrogen peroxide (0.52 ml, 27.5 wt %, 4.69 mmol, 4 equiv) was added to a solution of Intermediate 9 (0.53 g, 1.17 mmol) in THFlwater (4:1, 25 ml) at 0° C. under $N_2$. Stirred for 5 minutes then a 1M solution of Lithium hydroxide (1.17 ml, 1.17 mmol, 1 equiv) was added dropwise and stirred at 0° C. for 1 h. $Na_2SO_3$ solution (5 ml of 1M aqueous solution) was added and the reaction stirred for 5 mins. The bulk of the THF was removed under vacuum and 1M NaOH solution (5 ml) added. The aqueous layer was extracted with $CH_2Cl_2$ then acidified to pH6 with 10% HCl acid and extracted six times with $CH_2Cl_2$. The combined organic layers were dried over $MgSO_4$ and the solvent removed under vacuum to give the title comoound as a white solid (198 mg).

Intermediate 11

{4-t-butoxy-2(R)-(3-(4-pyridyl)propyl)succinyl}-L-β-cyclohexylalanine-N-( 2-phenylethyl)amide.

A solution of Intermediate 10 (198 mg, 0.68 mmol), L-β-cyclohexylalanine-N-( 2-phenylethyl)amide (186 mg, 0.68 mmol), N-methylmorpholine (68.7 mg, 74.7 μl, 0.68 mmol), 1-hydroxybenzotriazole (1.36 ml of a 0.5M solution in DMF, 0.68 mmol) and 1-(3-dimethylaminopropyl)-3-ethylcarbodiimide hydrochloride (130.4 mg, 0.68 mmol) in DMF (10 ml) was stirred under $N_2$ at room temperature for 18 h. After this time the reaction was partitioned between EtOAc and phosphate pH7 buffer. The aqueous layer was extracted twice with EtOAc and the combined organic layers washed with brine twice, dried over $MgSO_4$ and the solvent removed under vacuum to give a yellow oil which was purified on silica gel (Merck 9385) eluting with 5% MeOH/$CH_2Cl_2$ to give the title compound as a yellowish oil (397 mg).

$^1$Hnmr $CHCl_3$δ: 8.42 (dd, 2H); 7.31-6.90 (m, 9H); 4.43 (dd, 1H); 3.58- 3.41 (m, 2H); 2.82-2.53 (m, 5H); 1.79-0.75 (m, 19H); 1.42 (s, 9H).

Intermediate 12

{4-t-butoxy-2(R)-(3-(4-pyridyl)propyl)succinyl}-L-β-cyclohexylalanine-N-( 2-{p-sulphonamidophenyl)ethyl)amide By proceeding in a manner similar to Intermediate 11, but replacing the L-β-cyclohexylalanine-N-(2-phenytethyl)amide by L-β-cyctohexylalanine-N-[2-(p-sulphonamidophenyl)ethyl]amide, the title compound was obtained as an off-white powder.

$^1$Hnmr $CD_3OD$ δ:7.98 (s, 2H); 7.82 (d, 2H); 7.37 (d, 2H); 7.28 (d, 2H); 4.33 (m, 1H); 3.38 (m, 2H); 3.06-2.54 (m, 6H); 2.32 (dd, 1H); 1.83-0.78 (m 19H); 1.42 (s, 9H).

Example 1

[4-t-Butoxy-2(R)-(3-(2-phenoxyethyl)succinyl)-L-β-cyclohexylalanine-N-(2-phenylethyl)amide Ethyl chloroformate (196 μl, 222 mg, 2.04 mmol) 1.05 equiv) was added to a solution of intermediate 3 (600 mg, 2 mmol) and N-methytmorpholine (235 μl, 216 mg, 214 mmol, 1.1 equiv) in THF (10 ml) at −20° C. under a $N_2$ atmosphere. After 1 hour a solution of Intermediate 4 (532 mg, 1.94 mmol) in THF (5 ml) was added and the reaction allowed to warm to room temperature overnight. The reaction mixture was partitioned between EtOAc and water. The aqueous layer was extracted twice with EtOAc and then the combined organic layers were washed once with 10% HCl acid, once with brine and once with saturated sodium bicarbonate solution, dried over $MgSO_4$ and the solvent removed to give an oil which was purified on silica gel (Merck 9385) eluting with 1% MeOH/$CH_2Cl_2$ to give the title compound as a colourless oil (814 mg).

$^1$H NMR $CDCl_3$ δ: 7.33-6.87 (m, 10H); 6.18 (m, 2H); 4.35 (m, 1H); 3.96 (m, 2H); 3.41 (m, 2H); 2.92-2.66 (m, 3H); 2.43 (dd, 1H); 1.80-0.78 (m, 15H); 0.96 (s, 9H).

Example 2

{4-Hydroxy-2-(R)-(3-(2-phenoxyethyl)succinyl)-L-β-cyclohexylalanine-N-(2 2-phenylethyl)amide The compound of Example 1 (0.80 g, 1.45 mmol) was heated with water (1 ml) and TFA (4 ml) and stood overnight (18 hrs) at room temperature. The volatiles were removed under vacuum and the product was purified on silica gel (Merck 9385) eluting with EtOAc/hexane (1:1) to give 0.50 g of a powdery solid. 100 mgs of this were further purified by reverse phase hplc using TFA/$H_2O$/MeCN (staRRing with 0.1:50:50 ending with 0.1:0:100 over 20 minutes) to give 30 mgs of the title compound as a white solid.

$^1$H NMR $CD_3OD$ δ: 7.26-7.13 (m, 7H); 6.92-6.87 (m, 3H); 4.36 (dd, 1H); 3.97-3.93 (m, 2H); 2.99 (m, 1H); 2.72-2.65 (m, 3H); 2.50 (dd, 1H, J=16.7, 5.0 Hz); 2.03-0.83 (m, 17H).

Example 3

4-(N-Hydroxyamino)-2-(R)-(3-(2-phenoxyethyl)succinyl)-L-β-cyclohexylalanine-N-( 2-phenylethyl)amide Ethyl chloroformate (122 g, 108 μl ), 1.1 mmol, 1.4 equiv) was added to a −20° C. solution of the compound of Example 2 (398 mg 0.8 mmol) and N-methylmorpholine (123 mg, 132 μl, 1.2 mmol, 1.5 equiv) in THF (10 ml). The white suspension was stirred at −20° C. for 1 hr then O-trimethylsilylhydroxylamine (169 mg, 197 μl, 1.6 mmol, 2 equiv) was added and the solution allowed to warm to room temperature overnight. The reaction was partitioned between EtOAc and 10% HCl acid. The aqueous layer was washed twice with EtOAc and the combined organic layers washed once with brine and once with sodium bicarbonate solution, dried over $MgSO_4$ and the solvent removed under vacuum to give a white solid (316 mg), which was purified by reverse phase hplc using TFA/water/MeCN (starting with 0.1:50:50 and ending with 0.1:0:100 over 20 mins) to give the title compound as a white solid (142 mg)

$^1$H NMR $CD_3OD$ δ:7.25-7.13 (m, 7H); 6.91-6.87 (m, 3H); 4.32 (dd, 1H): 3.97-3.91 (m, 2H); 3.31 (m, 1H); 2.70 (t (app) J=7.2 Hz, 2H); 2.42 (dd, 1H); 2.27 (dd, 1H); 2.04-0.87 (m, 17H).

Example 4

{4-Hydroxy-2(R)-(3-(4-pyridinium)propyl)succinyl}-L-β-cyclohexylalanine-N-( 2-phenylethyl)amide trifluoroacetate A solution of Intermediate 11 (397 mg, 0.60 ml) in TFA (4ml) and water (1 ml) was stood at room temperature for 3 h. The volatiles were then removed under vacuum to give an oil which was purified on silica gel (Merck 9385) eluting with $CH_2Cl_2$/MeOH (9:1) to give the title compound as a colourless oil (328 g).

About 100 mg were further purified by reverse phase hplc eluting with TFNH$_2$O/MeOH (starting with 0.1:60:40 and ending with 0.1:40:60 over 20 mins).

$^1$Hnmr $CD_3OD$ δ:8.65 (d, 2H, J=6.4 Hz); 7.91 (d, 2H, J=6.5 Hz); 7.28- 7.15 (m, 5H); 4.36 (dd, 1H, J=5.3, 9.6 Hz); 3.49-3.28 (m, 2H); 2.99-2.59 (m, 4H); 2.39 (d, 1H, J=5.2, 16.9 Hz); 1.84-0.74 (m,19H).

$^{13}$Cnmr $CD_3OD$ δ: 176.8, 175.1, 174.9, 142.3, 140.4, 129.8, 129.5, 128.4, 127.4, 52.5, 41.9, 40.6, 37.6, 36.5, 36.4, 35.0, 34.8, 33.3, 33.1, 28.1, 27.6, 27.3, 27.0.

Example 5

{4-(N-hydroxyamino)-2(R)-(3-(4-pyridinium)propyl)succinyl}-L-β-cyclohexylalanine-N-( 2-phenylethyl)amide trifluoroacetate Ethylchloroformate (84.8 mg, 74.7 μl, 0.78 mmol, 2.1 equiv) was added to a cold (−20° C.) solution of the compound of Example 4 (225 mg, 0.37 mmol) and N-methyl morpholine (93.6 mg, 101.7 μl, 0.93 mmol, 2.5 equiv) in THF (5 ml) under $N_2$. Stirring was continued at −20° C. for 1 h then O-trimethylsilyloxyhydroxylamine (172 mg, 200 μl, 17 mmol, 4.6 equiv) was added and the reaction allowed to warm to room temperature and stirred overnight to give a white suspension, which was poured into saturated $NH_4Cl$ solution and extracted 3 times with EtOAc. The combined organic layers were washed once with brine, dried over $MgSO_4$ and solvent removed under vacuum to give a yellowish solid which was triturated with $CH_2Cl_2$/iPr$_2$O to give the title compound as an off white solid (225 gm).

About 70 mg were further purified by reverse phase hplc eluting with TFA/H$_2$O/MeCN (starting at 0.1:70:30 and ending with 0.1:50:50 over 20 mins) to give the title compound as a hygroscopic white solid (26.5 mg).

$^1$Hnmr δ $CD_3OD$: 8.66 (br s, 2H); 7.88 (d, 2H); 7.30-7.15 (m, 5H); 4.32 (dd, 1H); 3.49-3.34 (m, 2H); 3.03-2.71 (m, 5H); 2.41-2.16 (m, 2H);1.82-0.81 (m, 19H).

Example 6

{4-(N-hydroxyamino)-2-(R)-3-(N-methyl-4-pyridinium) propyl succinyl}-L-β-cyclohexylalanine-N-(2-phenylethyl)amide iodide The compound of Example 5 (48.0 mg, 0.08 mmol) was dissolved in 1 ml methyl iodide and stirred at room temperature for 18 h. The excess methyl iodide was removed by evaporation with $N_2$ and the resulting yellow gum was purified by reverse phase hplc eluting with TFA/H$_2$O/CH$_3$CN (starting with 0.1:70:30 and ending with 0.1:50:50 over 20 mins), to give the title compound as a hygroscopic gum (25 mg).

$^1$Hnmr $CD_3OD$ δ: 8.61 (d, 2H); 7.84 (d, 2H); 7.25-7.10 (m, 2H); 4.26 (m, 1H); 4.21 (s, 3H); 3.44-3.22 (m, 2H); 2.96-2.65 (m, 4H); 2.34-2.07 (m, 2H); 1.80-0.75 (m, 19H).

Example 7

[4-Hydroxy-2(R)-(3-(4-pyridinium)propyl)succinyl)-L-β-cyclohexylalanine-N-( 2-(p-sulphonamidophenyl)ethyl)amide trifluoroacetate By proceeding in a manner similar to Example 4 with Intermediate 12, the title compound was obtained as an off-white hygroscopic foam.

$^1$Hnmr $CD_3OD$ δ: 8.68 (d, 2H); 7.95 (d, 2H); 7.80 (d, 2H); 7.48 (d, 2H); 4.36 (m, 1H); 3.46 (m, 2H); 3.18-2.80 (m, 5H); 2.62 (dd, 1H); 2.51 (dd, 1H); 1.87-0.80 (m, 19H).

Example 8

{4-(N-Hydroxyamino)-2-(R)-(3-(4-pyridinium)propyl)succinyl}-L-β-cyclohexylalanine-N-( 2-(p-sulphonamidophenyl)ethyl)amide trifluoroacetate A solution of the compound of Example 7 (0.30 g, 0.44 mmol) in THF (5 ml) was treated with N-methylmorpholine (111 mg, 120 μl, 1.10 mmol), and cooled to −20° C. Ethyl chloroformate (50.4 mg, 44.4 μl, 0.46 mmol) was added and the resulting slurry stirred for 15 mins at −20° C. O-trimethylsilyl hydroxylamine (230 mg, 267 μl, 2.2 mmol) was then added and the reaction allowed to warm to room temperature over 18 hrs. The mixture was partitioned between EtOAc and phosphate pH7 buffer. The aqueous layer was extracted with EtOAc (x5) and the combined organic layers washed with brine then dried over $MgSO_4$, and solvent removed under vacuum to give a whitish solid, which was purified by reverse phase hplc (gradient elution over 20 mins TFA:water:MeCN 0.1:70:30 to 0.1:60:40) to give the title compound as a hygroscopic white solid (46 mg).

$^1$Hnmr $CH_3OD$ δ: 8.52 (br s, 2H); 8.14 (br d, 1H); 7.83 (br s, 1H); 7.75 (d, 2H); 7.47 (d, 2H); 4.31 (m, 1H); 3.46 (m, 2H); 3.04-2.74 (m,6H); 2.38 (d, 1H); 2.20 (d, 1H); 8.2-0.80 (m, 19H). .

We claim:

1. A compound of formula (1)

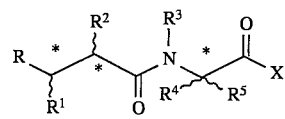

wherein R represents —CONHOH;

$R^1$ represents a hydrogen atom or an optionally substituted alkyl, alkenyl, aryl, aralkyl, heteroaralkyl or heteroarylthioalkyl group;

$R^2$ represents a heteroaralkyl, heteroaryloxyalkyl or heteroarylthioalkyl group;

$R^3$ represents a hydrogen atom or an alkyl group;

$R^4$ represents a hydrogen atom or an alkyl group;

$R^5$ represents an optionally substituted alkyl or alkenyl group optionally interrupted by one or more —O— or —S— atoms or —N($R^7$)— groups, where $R^7$ is a hydrogen atom or a $C_1$–$C_6$ alkyl group or a group —(Alk)$_m R^6$ where Alk is an alkyl or alkenyl group optionally interrupted by one or more —O— or —S— atoms or —N($R^7$) groups; n is zero or an integer 1, and $R^6$ is an optionally substituted cycloalkyl or cycloalkenyl group;

X represents an amino (—NH$_2$), or substituted amino, hydroxyl or substituted hydroxyl group;

or a salt, solvate, or hydrate thereof.

2. A compound of formula (1a)

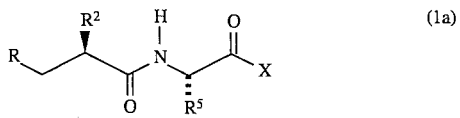

(1a)

wherein R represents —CONHOH;

$R^2$ represents a heteroaralkyl, heteroaryloxyalkyl or heteroarylthioalkyl group;

$R^5$ represents an optionally substituted alkyl or alkenyl group optionally interrupted by one or more —O— or —S— atoms or —N($R^7$)— groups, where $R^7$ is a hydrogen atom or a $C_1$–$C_6$ alkyl group or a group —(Alk)$_m R^6$ where Alk is an alkyl or alkenyl group optionally interrupted by one or more —O— or —S— atoms or —N($R^7$) groups; n is zero or an integer 1 and $R^6$ is an optionally substituted cycloalkyl or cycloalkenyl group;

X represents an amino (—NH$_2$), or substituted amino, hydroxyl or substituted hydroxyl group;

or a salt, solvate, or hydrate thereof.

3. A compound according to claim 1 wherein $R_1$, $R^3$ and $R^4$ is each a hydrogen atom.

4. A compound according to claim 1 wherein $R^2$ is an optionally substituted pyridinylalkyl or pyridinyloxyalkyl group.

5. A compound according to claim 1 wherein $R^5$ is a $C_{1-6}$ alkyl group or an AlkR$^6$ group, where Alk is a $C_{1-6}$ alkyl group and $R^6$ is a cycloalkyl or cycloalkenyl group.

6. A compound according to claim 1 where X is an amino or substituted amino group.

7. A pharmaceutical composition comprising a compound according to claim 1 and a pharmaceutically acceptable diluent, carrier or excipient.

8. {4-(Hydroxy-2(R)-(3-(4-pyridyl)propyl)succinyl}-L-β-cyclohexylalanine-N-( 2-phenylethyl)amide;

{4-(N-Hydroxyamino)-2(R)-(3-(4-pyridyl)succinyl)-L-β-cyclohexylalanine-N-( 2-phenylethyl)amide;

{4-(N-Hydroxyamino)-2(R)-(3-(N-methyl-4-pyridinium) propyl)succinyl)-L-β-cyclohexylalanine-N-(2-phenylethyl) amide iodide;

or a salt, solrate, or hydrate thereof.

* * * * *